US009681767B1

(12) United States Patent
Barker et al.

(10) Patent No.: US 9,681,767 B1
(45) Date of Patent: Jun. 20, 2017

(54) COMPRESSION STOCKING DONNING AID

(71) Applicant: Loren Charles Barker, Pratt, KS (US)

(72) Inventors: Loren Charles Barker, Pratt, KS (US); Gary Lewis Trimpe, Preston, KS (US)

( * ) Notice: Subject to any disclaimer, the term of this patent is extended or adjusted under 35 U.S.C. 154(b) by 0 days.

(21) Appl. No.: 15/368,745

(22) Filed: Dec. 5, 2016

Related U.S. Application Data

(60) Provisional application No. 62/262,675, filed on Dec. 3, 2015.

(51) Int. Cl.
*A47G 25/90* (2006.01)
*A61F 13/08* (2006.01)

(52) U.S. Cl.
CPC .......... *A47G 25/905* (2013.01); *A47G 25/90* (2013.01); *A61F 13/08* (2013.01)

(58) Field of Classification Search
CPC .... A47G 25/90; A47G 25/905; A47G 25/908; A61F 13/00; A61F 13/08
USPC .......................................................... D2/641
See application file for complete search history.

(56) References Cited

U.S. PATENT DOCUMENTS

| | | | | |
|---|---|---|---|---|
| 1,315,096 | A * | 9/1919 | Deiley | A47G 25/905 223/111 |
| 4,284,216 | A * | 8/1981 | Leland | A47G 25/905 223/111 |
| 4,756,453 | A * | 7/1988 | Pettit | A47G 25/905 223/111 |
| 5,357,830 | A * | 10/1994 | Mori | H02G 1/005 30/186 |
| 5,513,783 | A * | 5/1996 | White | A47G 25/905 223/111 |
| 7,395,951 | B2 * | 7/2008 | Clayman | A47G 25/905 223/111 |
| 7,988,022 | B1 * | 8/2011 | Hansson | A47G 25/905 223/111 |
| 2010/0286675 | A1 * | 11/2010 | Cho | A61B 17/2812 606/15 |
| 2014/0061260 | A1 * | 3/2014 | Kissel, Jr. | A47G 25/80 223/118 |

* cited by examiner

*Primary Examiner* — Ismael Izaguirre
(74) *Attorney, Agent, or Firm* — Martin S. High, P.C.

(57) ABSTRACT

Embodiments of the Compression Stocking Donning Aid are comprised of a handle assembly, a bracket assembly, and a sock applicator assembly. The handle assembly is comprised of two, mirror image handles that are covered by handle grips. The handles are essentially linear elongated cylinders that allow the user of the Aid to grasp the Aid and apply the necessary leverage to open the compression stocking for application. The sock applicator assembly is comprised of two sock applicators. The bracket assembly is comprised of a back plate, a front plate, a ratcheting plate, a ratcheting dog, a pivot fastener, a ratcheting dog fastener, and padding. The ratcheting plate forms ratcheting teeth that engage with the ratcheting dog while the handles are moved inward.

4 Claims, 4 Drawing Sheets

COMPRESSION STOCKING DONNING AID

STATEMENT REGARDING FEDERALLY SPONSORED RESEARCH OR DEVELOPMENT

Not applicable

BACKGROUND OF THE EMBODIMENTS

Field of the Embodiments

The general field of the embodiments of the Compression Stocking Donning Aid is the field of clothing donning. More specifically the embodiments relate to compression stocking aid systems.

Description of Prior Art

Compression socks are notoriously difficult for a user to don. Elderly, infirm or injured individuals may have difficulty reaching or bending down to place a sock or stocking on the foot. Even strong and healthy individuals are challenged by putting on compression socks. This difficulty may be caused by back problems, arthritis, age, or as the result of a recent surgery. The donning of a sock or stocking generally requires the individual to correctly align the sock and the foot, open the sock, insert the foot and pull the sock over the foot. Some or all of these tasks may require some degree of assistance for the elderly or infirm. Further, it is extremely difficult for another person to put on compression socks on a patient as the leverage to pull the socks on is not available to the helper.

Various attempts have been made to solve problems found in clothing donning art. Among these are found in: U.S. Pat. App. Pub. Nos. and U.S. Pat. No. 5,799,844 to James, U.S. Pat. No. 6,598,769 to Franco, U.S. Pat. No. 8,215,524 to Swisher, U.S. Pat. No. 8,418,896 to Higa, 2004/0069820 to Van Loef, and 2004/0149789 to Landsberger et al. These prior art references are representative of devices used to aid in the donning of socks. None of the above inventions and patents, taken either singly or in combination, is seen to describe the invention as claimed.

The prior art includes various devices have been employed to aid such individuals in their attempts to put on socks or stockings. However, some devices are difficult for a user to adequately pull with enough force to put on the sock or use straps which can be difficult for a user to reach or to maintain an adequate grasp. Also, other devices can excessively stretch the sock such that the life of the sock or stocking is reduced. Therefore, a suitable solution is desired. Collectively, a need exists for a reliable compression stocking aid system to avoid the above-mentioned problems.

SUMMARY OF THE EMBODIMENTS

Embodiments of the Compression Stocking Donning Aid are comprised of a handle assembly, a bracket assembly, and a sock applicator assembly. The handle assembly is comprised of two, mirror image handles that are covered by handle grips. The two handles are weldedly connected to the bracket assembly. The handles are essentially linear elongated cylinders that allow the user of the Aid to grasp the Aid and apply the necessary leverage to open the compression stocking for application. The sock applicator assembly is comprised of two sock applicators. The sock applicators are each comprised of cylinders formed in a "S" shaped curve terminated with end terminators. The bracket assembly is comprised of a back plate, a front plate, a ratcheting plate, a ratcheting dog, a pivot fastener, a ratcheting dog fastener, and padding. The back plate and a front plate are identical in shape. The ratcheting plate forms ratcheting teeth that engage with the ratcheting dog while the handles are moved inward to provide intermediate stopping points along the range of motion of the handles when the handles are compressed, thus expanding the compression stocking. When the entire Compression Stocking Donning Aid is inverted, the ratcheting dog is disengaged from the ratcheting teeth allowing the handles to be expanded and readied for the next use.

There has thus been outlined, rather broadly, the more important features of the embodiments in order that the detailed description thereof that follows may be better understood, and in order that the present contribution to the art may be better appreciated. There are, of course, additional features of the embodiments that will be described hereinafter and which will form the subject matter of the claims appended hereto.

In this respect, before explaining at least one embodiment of the embodiments in detail, it is to be understood that the embodiment is not limited in this application to the details of construction and to the arrangements of the components set forth in the following description or illustrated in the drawings. The embodiment or embodiments are capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be used as a basis for the designing of other structures, methods and systems for carrying out the several purposes of the embodiments. Additional benefits and advantages of the embodiments will become apparent in those skilled in the art to which the present embodiments relate from the subsequent description of the preferred embodiment and the appended claims, taken in conjunction with the accompanying drawings. It is important, therefore, that the claims be regarded as including such equivalent constructions insofar as they do not depart from the spirit and scope of the embodiments.

Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application. The abstract is neither intended to define the embodiments of the application which is measured by the claims, nor is it intended to be limiting as to the scope of the embodiments in any way.

DETAILED DESCRIPTION OF THE PREFERRED EMBODIMENTS

Figure 1:
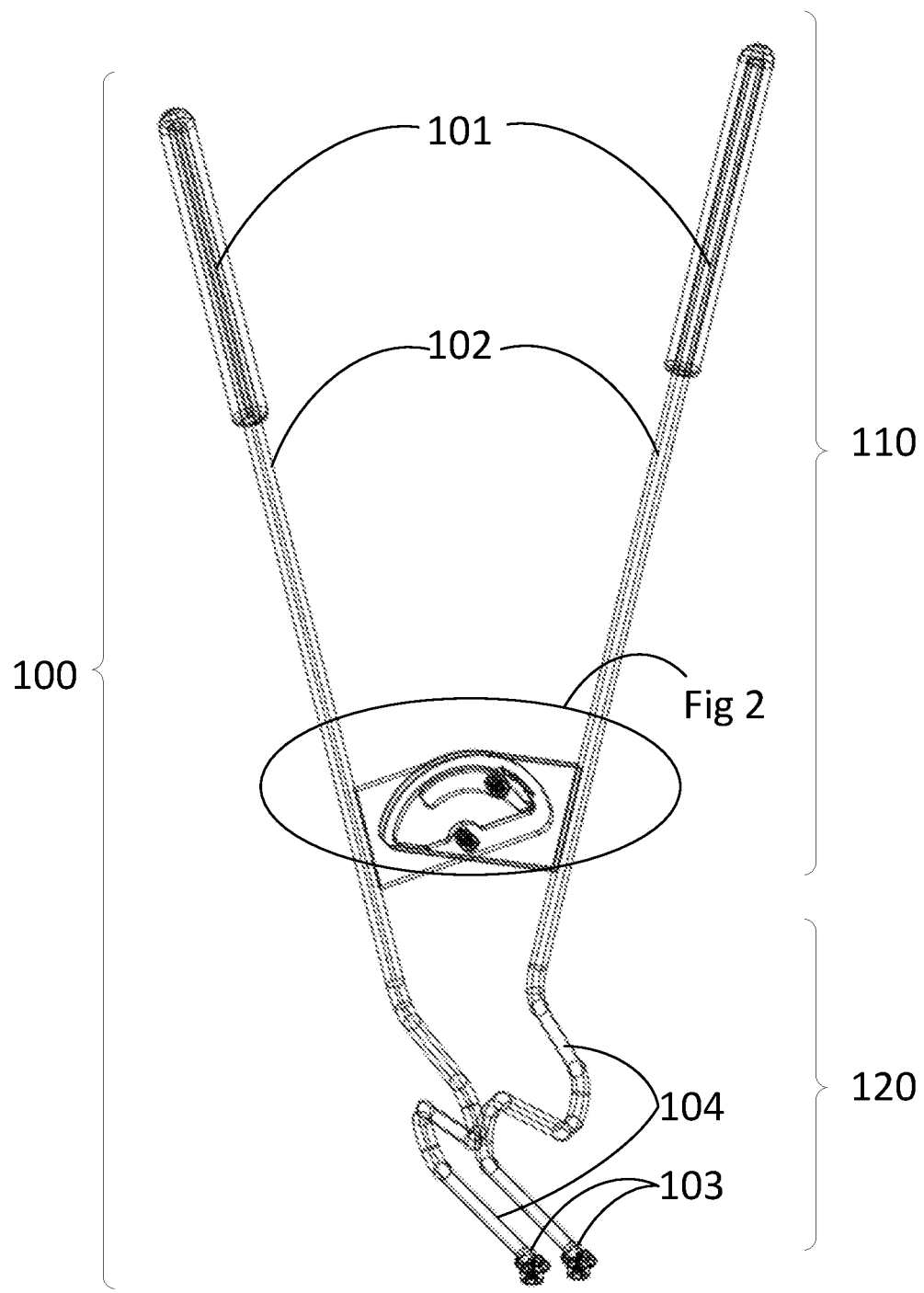
FIG. 1 is a perspective view of an embodiment of the Compression Stocking Donning Aid 100.
Figure 2:
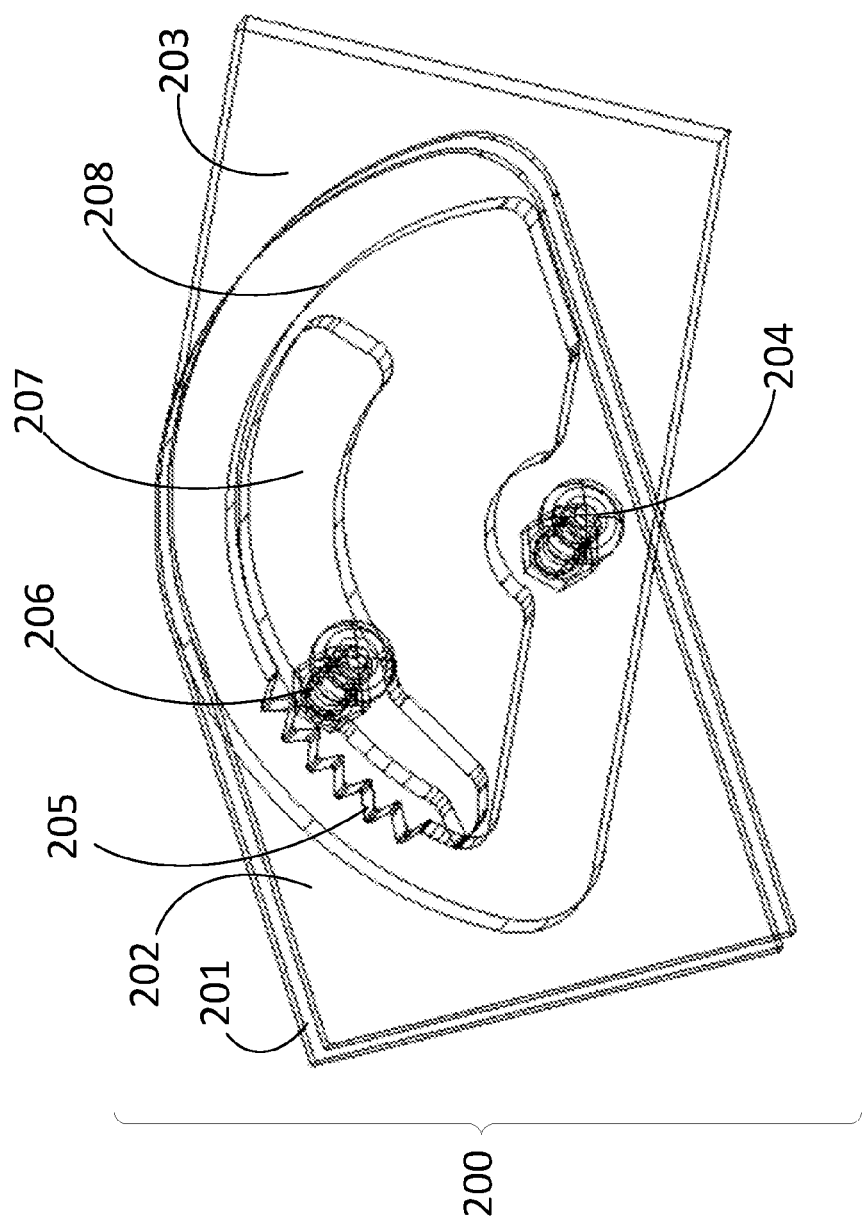
FIG. 2 is an expanded view of an embodiment of the Compression Stocking Donning bracket assembly 200 of the Compression Stocking Donning Aid 100.
Figure 3:
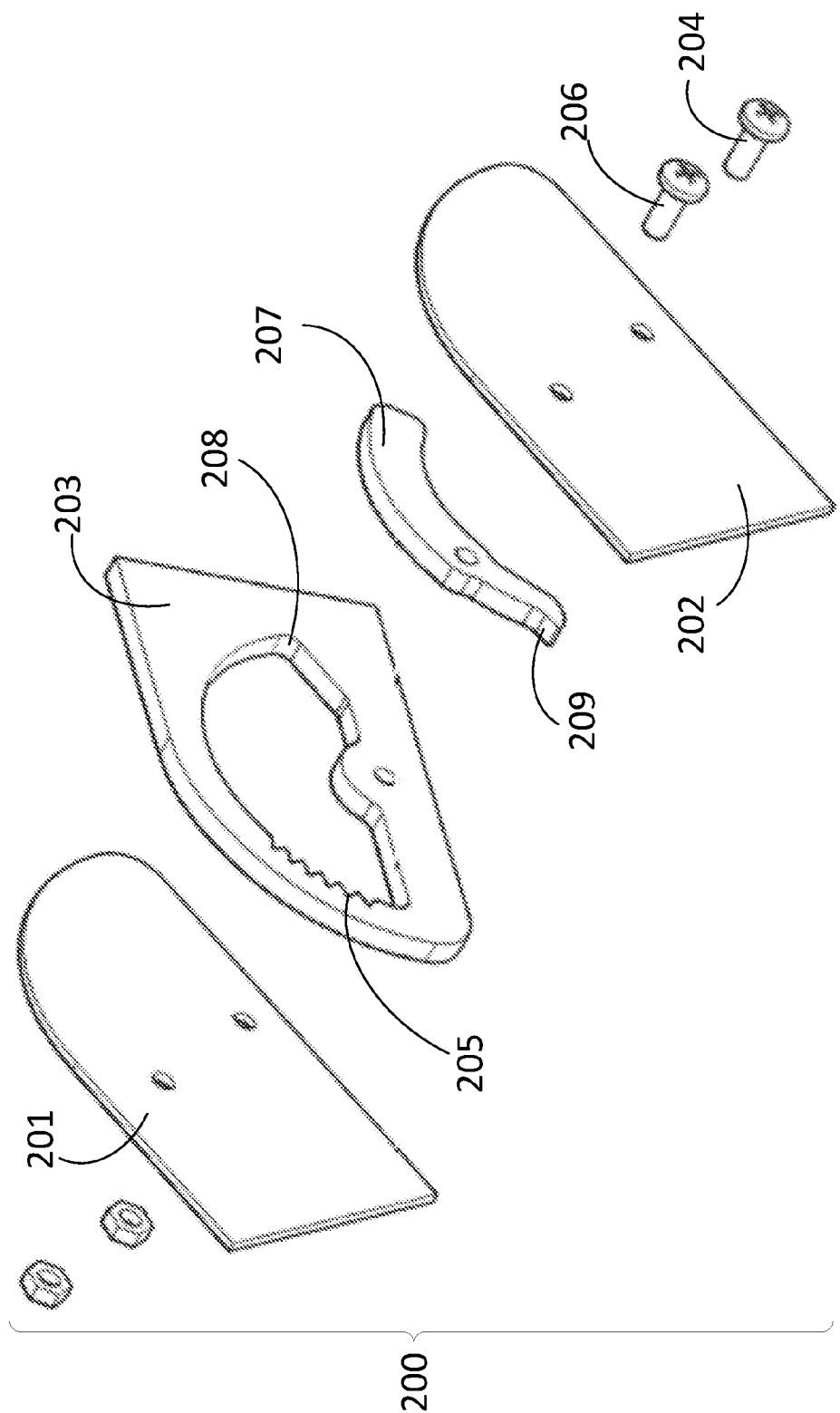
FIG. 3 is an exploded view of an embodiment of the bracket assembly 200 of the Compression Stocking Donning Aid 100.
Figure 4:
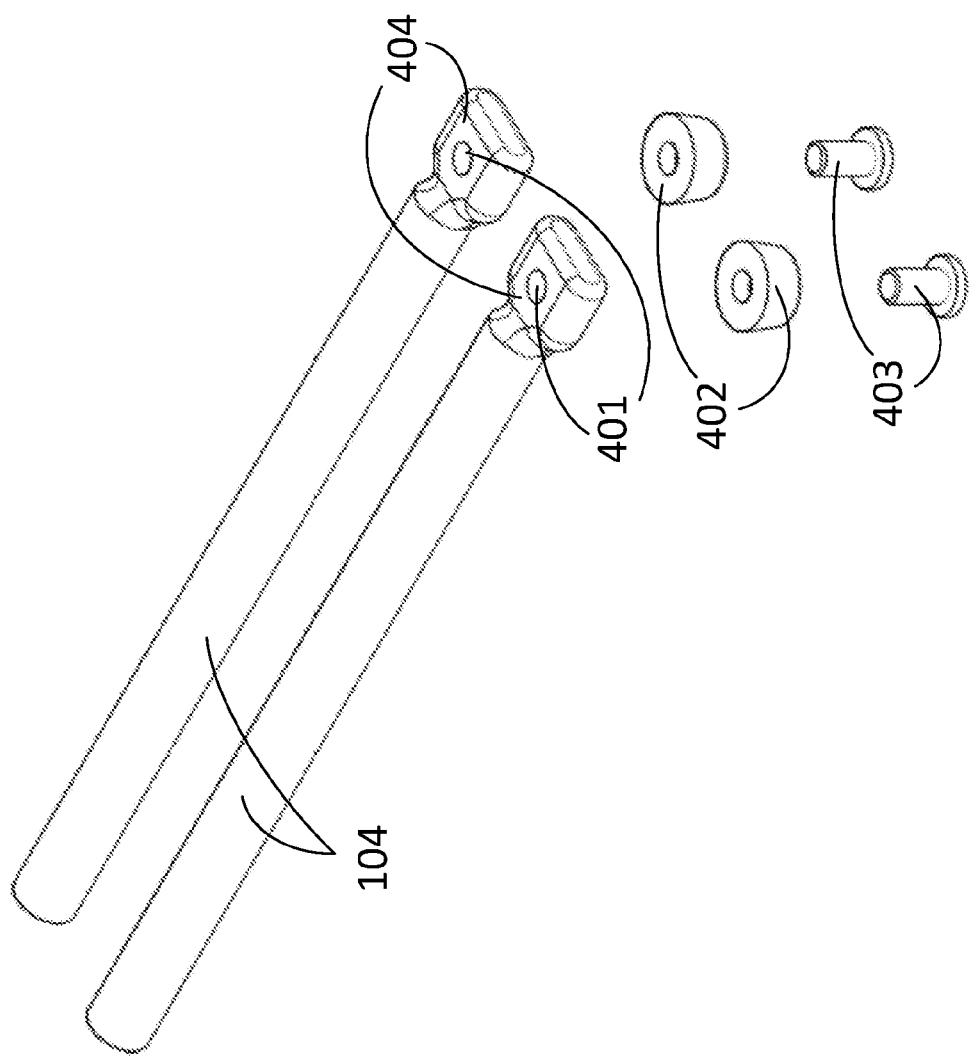
FIG. 4 is an exploded view of an embodiment of the end terminators 103 of the Compression Stocking Donning Aid 100.

Embodiments of the Compression Stocking Donning Aid 100 ("Aid") are comprised of a handle assembly 110, a bracket assembly 200, and a sock applicator assembly 120.

The handle assembly 110 is comprised of two, mirror image handles 102 that are covered by handle grips 101. The two handles 102 are weldedly connected to the bracket assembly 200. The handles are essentially linear elongated cylinders that allow the user of the Aid 100 to grasp the Aid and apply the necessary leverage to open the compression stocking for application. The handles 102 are comprised of ⅜" cold rolled steel rods and covered with 7" black closed cell vinyl foam grips with a wall thickness of 0.12" to 0.15" to insulate, cushion, and aid in gripping and compressing the handles 102.

The sock applicator assembly 120 is comprised of two sock applicators 104. The sock applicators 104 are each comprised of cylinders formed in a "S" shaped curve terminated with end terminators 103. The sock applicators 104 are comprised of ⅜" cold rolled steel rods and integral to the handles 102. A handle 102 and its integral sock applicator 104 are essentially planar. At the end of the sock applicators 104, the steel rod forms a flattened end 404 and a threaded aperture 401 in the flattened end 404. The end terminators 103 are attached to the sock applicators via a fastener and the threaded aperture 401. In an embodiment the end terminators 103 are ⅞" wide by ½" high rubber tips 402 that prevent the device from slipping on the floor when the user inserts their foot. The rubber tips 103 are secured to the end of sock applicators 104 with a fastener 403 that is flush to the sock applicators 104.

The bracket assembly 200 is comprised of a back plate 201, a front plate 202, a ratcheting plate 203, a ratcheting dog 207, a pivot fastener 204, a ratcheting dog fastener 206, and padding. The bracket assembly 200 is constructed of steel and weldedly affixed to the handles 102 as described further below.

The back plate 201 and a front plate 202 are identical in shape. The back plate 201 and the front plate 202 are essentially rectangular plates but with one end of the plates linear and the other end of the plates curved. The straight ends of the back plate 201 and a front plate 202 are weldedly affixed to one of the handles 102 allowing an interior gap between the two plates. The interior gap between the back plate 201 and a front plate 202 provides a path for the ratcheting plate 203 to slide as the handles 102 are moved inward and outward. The back plate 201 and the front plate 202 move together as the handles 102 are opened and closed.

The ratcheting plate 203 is essentially rectangular shaped with one end of the plate linear and the other end of the plate curved. The ratcheting plate 203 is comprised of and forms ratcheting teeth 205 that engage with the ratcheting dog 207 while the handles 102 are moved inward relative to each other to provide intermediate stopping points along the range of motion of the handles 102 when the handles are compressed. This is what causes the compression stocking to expand. The straight end of the ratcheting plate 203 is weldedly affixed to one of the handles. As discussed in more detail below, when the entire Aid is inverted, the ratcheting dog 207 is disengaged from ratcheting teeth 205 allowing the handles to be expanded and readied for the next use. The ratcheting dog 207 is affixed via the ratcheting dog fastener 206 which passes through the back plate 201 and the front plate 202. The opening 208 formed by the ratcheting plate 203 allows the ratcheting dog 207 to move freely between the back plate 201 and front plate 202.

The pivot fastener 204 passes through the back plate 201, the front plate 202, and the ratcheting plate 203 to secure all three plates together. The pivot fastener 204 allows the ratcheting plate 203 to move around the axis provided by the pivot fastener 204 and independently from the back plate 201 and the front plate 202.

The side of bracket assembly 200 that faces the user's shins will be covered with padding. This padding is comprised of ¼" thick foam rubber bumper with adhesive backing and is constructed of black closed cell crosslinked polyethylene foam. The purpose of the padding is to protect a user's shins in the event the user moves their foot through the sock and contacts the bracket assembly 200. The padding will form apertures to allow for the bolts to fit flush with the padding. The padding will comprise one or more stickers containing product and marketing information.

The bracket assembly 200 serves as the fulcrum for the two handles 102. As the user pushes the handles 102 towards each other, the sock applicators 104 are forced outward, the compression stocking is expanded allowing the user to insert his foot. The bracket assembly 200 securely opens and locks the sock applicators 104 to allow the user to insert their foot into the sock without slippage.

The center of gravity of the ratcheting dog 207 is offset from the location of the ratcheting dog fastener 206. When the Aid 100 is upright, with the sock applicator assembly 120 located on or near the ground, the ratcheting dog 207 is engaged with the ratcheting teeth 205. When the Aid 100 is inverted, the ratcheting dog 207 is disengaged with the ratcheting teeth 205. The shape of the pawl 209 of the ratcheting dog 207 is shaped so that as the handles are compressed towards each other the pawl 209 slides over the teeth, but engages with the ratcheting teeth 205 and prevents backward motion. This allows the ratcheting teeth 205 and pawl 209 to allow for intermediate stopping points as the compression stocking is expanded. When the Aid 100 is turned upside down, the ratcheting teeth 205 disengage with the ratcheting dog 207 allowing the handles to open thereby readying the Aid 100 for the next use.

In an embodiment of the Aid 100 all of the metallic materials are zinc dip coated.

To use the Aid 100, the user disengages the ratcheting dog 207 from the ratcheting teeth 205 by inverting the Aid 100, which allows gravity to drop the pawl 209 away from the ratcheting teeth 205 and allows the user to expand the handles 102, which simultaneously brings the sock applicators 104 together. A compression stocking is then placed over the bottom portion of the sock applicators 104 of the sock assembly 120. The user then compresses the handles 102 to expand the sock applicator assembly 120 and the compression stocking. As the handles 102 are compressed, the pawl 209 on the ratcheting dog 207 engages with successive ratcheting teeth 205 which locks the handles 102 and the sock applicator assembly 120 in place. Additional pressure on the handles 102 causes the sock applicator assembly 120 to expand further and causes the pawl 209 on the ratcheting dog 207 to lock the expansion temporarily in place. The user easily inserts their foot into the compression sock and presses their foot forward through the sock until the sock slips entirely off the sock applicators 104 onto the foot. The user then sets the Aid 100 aside and rolls the compressing stocking upward and over the calf.

What is claimed is:

1. A compression stocking donning aid comprised of a handle assembly, a bracket assembly, and a sock applicator assembly wherein the handle assembly is comprised of two, mirror image handles that are covered by handle grips; wherein the two handles are weldedly connected to the bracket assembly; wherein the sock applicator assembly is comprised of two sock applicators; wherein the sock applicators are each comprised of steel rods formed in a "S" shaped curve terminated with end terminators; wherein the ends of the sock applicators form flattened ends and form threaded apertures; wherein the end terminators are attached to the sock applicators via a fastener and the threaded aperture.

2. The compression stocking donning aid in claim 1 wherein the sock applicators are each comprised of cylinders formed in a "S" shaped curve terminated with end terminators; wherein the sock applicators are integrally connected to the handles; and wherein each handle and its integrally connected sock applicator are essentially planar.

3. The compression stocking donning aid in claim 1 wherein the bracket assembly is comprised of a back plate, a front plate, a ratcheting plate, a ratcheting dog, a pivot fastener, a ratcheting dog fastener, and padding.

4. The compression stocking donning aid in claim 3 wherein the back plate and the front plate are identical in shape; wherein the back plate and the front plate are essentially rectangular plates but with one end of the plates linear and the other end of the plates curved; wherein the straight ends of the back plate and a front plate are weldedly affixed to one of the handles allowing an interior gap between the two plates.

* * * * *